US007149631B2

(12) United States Patent
Brenner et al.

(10) Patent No.: US 7,149,631 B2
(45) Date of Patent: Dec. 12, 2006

(54) ALTERNATIVE SPLICING AND NONSENSE-MEDIATED DECAY: COMPUTATIONAL METHODS AND GENE REGULATION

(75) Inventors: Steven E. Brenner, Oakland, CA (US); Richard E. Green, Berkeley, CA (US); Benjamin P. Lewis, Berkeley, CA (US)

(73) Assignee: Regents of the University of California, Oakland, CA (US)

( * ) Notice: Subject to any disclaimer, the term of this patent is extended or adjusted under 35 U.S.C. 154(b) by 524 days.

(21) Appl. No.: 10/159,997

(22) Filed: May 31, 2002

(65) Prior Publication Data

US 2003/0228578 A1 Dec. 11, 2003

(51) Int. Cl.
*G01N 33/48* (2006.01)
*G06F 19/00* (2006.01)

(52) U.S. Cl. .......................................... 702/19; 702/20
(58) Field of Classification Search .................. 702/19, 702/20
See application file for complete search history.

(56) References Cited

OTHER PUBLICATIONS

Honkura et al., Nucleic Acids Research, vol. 30, pp. 221-225, Jan. 2002.*
Sun et al., The EMBO Journal, vol. 19, pp. 4734-4744, 2000.*

\* cited by examiner

*Primary Examiner*—Tim Vo
*Assistant Examiner*—Cheyne D. Ly
(74) *Attorney, Agent, or Firm*—Richard Aron Osman

(57) ABSTRACT

Computational methods identify alternate splice forms of known gene transcripts and isoforms that are subject to NMD (nonsense-mediated decay). These methods were used to identify thousands of human genes that generate alternative splice forms, and to demonstrate that about a third of these are subject to NMD. This high prevalence of NMD-targeted transcripts indicates a systemic way of regulating gene expression—by shunting gene expression to nonproductive splice variants. This endemic regulation is exploited to engineer regulation of gene expression, to characterize splice pathway components and to assay splice environments, for example, using NMD-regulated reporter genes.

4 Claims, 3 Drawing Sheets
(3 of 3 Drawing Sheet(s) Filed in Color)

Splice inference

Alternative splice pairs, by mode and coverage

Alternative isoform inference from splice pairs

Isoforms of alternatively spliced RefSeq-coding genes

ALTERNATIVE SPLICING AND NONSENSE-MEDIATED DECAY: COMPUTATIONAL METHODS AND GENE REGULATION

This invention was made with Government support under Grant Nos. 732-HG000747 and 1-K22-HG00056 awarded by the National Institutes of Health. The Government has certain rights in this invention.

INTRODUCTION

1. Field of the Invention

The field of the invention is computational and molecular methods relating to gene regulation by alternative splicing and nonsense-mediated decay.

2. Background of the Invention

Although studies have shown that alternative splicing plays a major role in generating protein diversity, standard analyses may not provide a full appreciation of how alternative splicing modulates gene function. Due to the limitations of the ESTs from which alternative splicing information is commonly derived, researchers often restrict their analyses to the simplest splicing modes: exon skipping and mutually exclusive exon usage. Similarly, researchers commonly dismiss alternative transcripts that code for early translational termination, since those mRNAs are deemed incapable of generating a functional product. A more complete understanding of alternative splicing requires an unbiased consideration of all alternative mRNA isoforms.

mRNA surveillance, or nonsense-mediated decay (NMD) is a surveillance mechanism for clearing the cell of transcripts that contain premature termination codons. Prior to the present invention, this system was presumed to be of limited physiological relevance, because it was shown to be not essential for viability in yeast and nematodes, and functional genetic knock-outs exhibit only mild phenotypes (e.g. Mitrovich et al., 2000, Genes & Development 14, 2173-84). To the contrary, we find that this systems is widely used to regulate gene expression, and cells provide a vast and varied repertoire of endogenous splicing reagents which regulate gene expression by generating NMD-targeted isoforms. This invention harnesses these systems and reagents to predict and to engineer target gene expression.

SUMMARY OF THE INVENTION

The invention provides computational methods to identify alternate splice forms of known gene transcripts and isoforms that are subject to NMD (nonsense-mediated decay), an endogenous surveillance mechanism for clearing the cell of transcripts that contain premature termination codons. These methods were used to identify thousands of human genes that generate alternative splice forms, and to demonstrate that about a third of these are subject to NMD. This high prevalence of NMD-targeted transcripts indicates a systemic way of regulating gene expression—by shunting gene expression to nonproductive splice variants. The invention exploits this endemic regulation to engineer regulation of gene expression, to characterize splice pathway components and to assay splice environments, for example, using NMD-regulated reporter genes.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF PARTICULAR EMBODIMENTS OF THE INVENTION

Figure 1A:
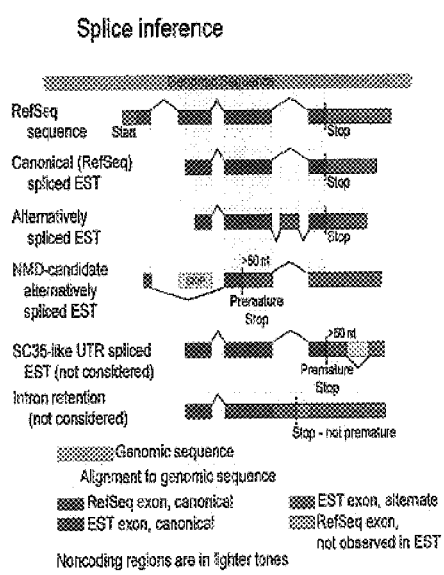
FIG. 1a diagrams alternative splice detection and classification: Splice inference.

The following descriptions of particular embodiments and examples are offered by way of illustration and not by way of limitation.

I. Computational Methods for Identifying Alternative Splice Forms of Known Genes and Assuring the Reliability of Inferred Splicing Events We have developed a protocol to systematically identify alternative mRNA isoforms of known human genes. This protocol provides a system of rules for identifying target gene sequences by mapping mRNA sequences to genomic sequences and then identifying alternate mRNA splice isoforms of the target gene sequences by aligning EST sequences to the target gene sequences and using a transcript assembly protocol.

Accordingly, the invention provides a computational method for systematically identifying alternative mRNA splice isoforms of known genes, the method comprising the steps of:

a) identifying target gene sequences by mapping mRNA sequences of an mRNA sequence dataset to genomic sequences of a genomic DNA sequence dataset, wherein:

each mRNA sequence is required to align to a corresponding genomic sequence over the full length of the coding sequence of the mRNA sequence, without gaps in the exons of the genomic sequence;

at least 98% identity between each mRNA sequence and the corresponding genomic sequence is required, favoring the mRNA sequence in case of nucleotide mismatch; and preferably, only the mRNA sequence containing the largest number of exons is used when multiple mRNA sequences align to the same genomic sequence; and b) identifying a dataset of alternate mRNA splice isoforms of the target gene sequences by aligning EST sequences from an EST sequence dataset to the target gene sequences and using a transcript assembly protocol, wherein:

the isoform dataset is restricted to mRNA sequences in which the 5' end of an EST sequence aligns to a coding sequence of the corresponding mRNA sequence, such that the reading frame of the coding sequences can be determined for all isoforms of the dataset, and isoforms presenting intron retention are excluded from the dataset, and coverage by multiple EST sequences is required or at least used as a confidence metric for each splicing event.

In a particular application, the known genes are human genes, the mRNA database is RefSeq (Pruitt, et al., *Nucleic*

*Acids Research* 29, 137–140 (Jan. 1, 2001)), the genomic database is NCBI's human genome database (Lander et al., *Nature* 409, 860–921 (Feb. 15, 2001), and the EST database is dbEST (Boguski, et al., *Nature Genetics* 4, 332–333 (August 1993). A particular transcript assembly protocol is TAP (Kan, Rouchka, Gish, States, *Genome Research* 11, 889–900 (2001). In an exemplary implementation of this protocol, we map mRNAs from the RefSeq database to contig sequences from the NCBI human genome, requiring that an mRNA align to genomic sequence over the full length of the coding sequence, without gaps in the exons. We further require 98% identity between the sequences, favoring RefSeq sequence in cases of nucleotide mismatch. When multiple RefSeq mRNAs align to the same region of genomic sequence, we use only the mRNA containing the largest number of exons. To detect alternate isoforms, we align EST sequences from dbEST to the genomic sequence and use TAP to infer alternate mRNA splice forms from these alignments. Since we use known genes, the reading frame of the primary mRNA isoforms (i.e., the RefSeq mRNAs) is known. So that the reading frame can be determined for all EST-suggested alternate isoforms, we restrict our set to cases in which the 5' end of the EST sequences align to coding sequences of the RefSeq mRNA. We also exclude cases of intron retention, as these are indistinguishable from incompletely-processed transcripts, a common dbEST contaminant. We have higher confidence in splicing events with coverage by multiple ESTs as these are less likely to result from experimental artifacts in dbEST.

Files within the /src directory of compact disc #1 submitted herewith and incorporated herein, provide exemplary code for implementing this protocol.

II. Identification of Thousands of Human Genes that Generate Alternative Splice Forms In an exemplary implementation, the protocol described in (I) was used to identify 2226 human genes that undergo alternative splicing to generate 5803 distinct mRNAs.

Accordingly, the invention provides isolated and/or recombinant alternatively spliced isoforms of these genes. Such isoforms may be unambiguously described in alternative ways. For example, a given isoform may be described in terms of a defined splice junction at a defined position, in terms of a particular truncation or excision (e.g. excision of exon X); in terms of a defined exon—exon splice junction, in terms of a recited nucleotide sequence, etc. For example, the file Alt_and_NMD_isoform_list.txt, provided on compact disc #1 submitted herewith and incorporated herein, defines isoforms by providing for each recited nucleotide sequence.

III. Computational Methods for Identifying mRNA Isoforms that are Subjected to NMD We have extended the protocol from (I) to systematically identify cases in which alternative splicing generates targets for NMD. This protocol provides a system of rules for identifying isoform targets of NMD, e.g. when an alternative splice found by this protocol is observed to introduce a stop codon more than 50 bp upstream of the final exon-exon splice junction of an inferred mRNA isoform, the stop codon is classified as being premature and the corresponding mRNA isoform is an apparent target of NMD.

Accordingly, the invention also provides a computational method, comprising the step of identifying a subset of an isoform dataset consisting of isoforms subject to nonsense-mediated decay (NMD), comprising: screening the isoform dataset for a subset of isoforms comprising alternate splices which introduce a stop codon more than 50 bp upstream of the final exon-exon splice junction, and classifying such subset isoforms as comprising premature stop codons and as targets of NMD.

Programs in /src provided on compact disc #1 submitted herewith and incorporated herein, provide exemplary code for implementing this protocol.

IV. Identification of Hundreds of Human Genes that Naturally Generate Splice Forms that are Apparent Targets of NMD Using the method described in (III), we identified 769 human genes that undergo alternative splicing to generate 1213 prematurely-terminating alternative mRNAs that are apparent targets of NMD.

Accordingly, the invention provides isolated and/or recombinant alternatively spliced, NMD-targeted isoforms of these genes. Such isoforms may be unambiguously described in alternative ways. For example, a given isoform may be described in terms of a defined splice junction at a defined position, in terms of a particular truncation or excision (e.g. excision of exon X); in terms of a defined exon—exon splice junction, in terms of a recited nucleotide sequence, etc. For example, Alt_and_NMD_isoform_list.txt, provided on compact disc #1 submitted herewith and incorporated herein, defines isoforms by providing for each a recited nucleotide sequence.

V. Experimental Approaches for Identifying Which Isoforms of a Gene Will be Expressed We use techniques for measuring gene expression, such as DNA microarray hybridization analyses, to determine under what conditions each isoform of a gene is expressed. Coupled with knowledge of which isoforms are targeted for NMD (supra), this method provides accurate determination of protein expression.

Accordingly, the invention provides using isoform expression analysis to predict protein expression (e.g. using microarrays to define NMD-targeted isoform expression conditions and from there predict protein expression), particularly in large-scale analyses, across many genes. For example, the invention provides a method of analyzing isoform expression to determine protein expression across a panel of divergent genes, said method comprising the steps of:

(a) determining isoform expression across a large-scale panel of divergent genes;
(b) correlating the expressed isoforms with NMD-mediated regulation; and
(c) inferring from the correlating step protein expression of each gene.

VI. Control of Protein Expression by the Manipulation of Splicing Factors

We demonstrate that genes can be generally and predictably engineered to undergo alternative splicing, so that multiple mRNA isoforms are generated. Engineered alternative splicing can be regulated in any of the ways that alternative splicing is regulated in vivo: addition or subtraction of known alternative splicing factors, changing concentration of basal splicing factors, etc. One or more of the isoforms can be engineered to contain premature termination codons causing these mRNAs to be selectively degraded. In this way, under prescribed conditions, engineered genes can be tightly regulated. Accordingly, the novel isoforms disclosed herein provide myriad reagents, including sites, splice junctions and splice environments, with pre-determinable effects on target gene expression regulation. While precise effects are best confirmed empirically, native expression patterns of the natural target gene provide preliminary guidance for predetermining heterologous expression regulation. A particular advantage of this post-transcriptional regulation is that it can make use of endogenous splicing factors to control expression, making the method particularly well-suited for in vivo applications. Hence, this method is useful for studying the function of specific genes and proteins in cell culture, and for generating transgenic animals in which expression of exogenous genetic material is limited to certain cell types based on their splicing environment.

Accordingly, the invention provides engineering target genes to undergo alternative splicing, so that multiple mRNA isoforms, including one or more NMD-targeted isoforms, are generated, and thereby providing predetermined NMD-mediated, postranscriptional expression regulation of the gene. In a particular embodiment, the invention provides a method for regulating gene expression comprising the steps of:

genetically engineering in a target gene a change in the native pattern of splice junctions to provide at least a predetermined first, non-natural NMD-targeted splice form and a predetermined second, non-NMD-targeted splice form, wherein expression of the gene is regulated by the relative expression of the first and second splice forms; and
  detecting or inferring the relative expression of the first and second splice forms.

VII. Assay of Splice Environment

Engineered reporter constructs can be made in such a way that one isoform expresses a reporter protein and the other is a target for nonsense-mediated decay. Transgenic animals or cultured tissue naturally make splicing decisions based on presence, absence, or abundance of splicing factors. The reporter, then, indicates that a specific splicing decision has been made over another. Because many basic biological processes are regulated by changes in splice environment (sex-determination, organ development, cancer, etc.) this method provides an important tool for exploiting and manipulating these processes. Exploiting our finding that NMD-regulated gene expression occurs across such large numbers of cell-types, this approach may be implemented in a high-throughput manner using, for example, fluorescent probe reporters and Fluorescence-Activated Cell Sorting (FACS).

Accordingly, the invention provides NMD-regulated reporter constructs to report specific splicing decisions, particularly wherein large numbers of different splice environments are assayed in parallel, such as in a transgenic animal or in a high-throughput drug screen.

Accordingly, the invention also provides a method of assaying splice environments, said method comprising the steps of:

providing reporter construct providing at least a predetermined first NMD-targeted splice form and a predetermined second, non-NMD-targeted splice form;
  expressing said construct in a panel of diverse cell types, wherein production of the first and second splice forms is splice-environment dependent and yields a splice-form dependent signal; and
  detecting said splice-form dependent signal in each cell of the panel as an indication of the splice environment.

Similarly, the invention also provides a construct for reporting non-constitutive, splice-dependent, NMD-targeted gene expression, said construct comprising a reporter sequence and alternative splice sites, whereupon expression of the construct the splice sites recombine to provide at least a predetermined first NMD-targeted splice form and a predetermined second, non-NMD-targeted splice form, wherein production of the first splice form is non-constitutive, splice-environment dependent and yields a splice-form dependent signal of expression of the reporter sequence, particularly wherein production of both the first and second splice form is non-constitutive, splice-environment dependent and yields a splice-form dependent signal of expression of the reporter sequence. Constitutive splice forms result from ubiquitously-expressed splice factors, as opposed to splice factors differentially expressed according to cell-type, developmental stage, or environmental conditions.

VIII. Experimental Probe of Cis-Acting Splicing Factors

We show that engineered reporter genes with a variety of potential cis splicing elements may be used to experimentally probe the functional roles of specific splicing signals. Current methods rely on in vitro splicing reactions and/or RT-PCR assays, both of which are prone to experimental artifact. Our approach may also be implemented in a high-throughput manner using, for example, fluorescent probe reporters and Fluorescence-Activated Cell Sorting (FACS).

Accordingly, our invention provides engineering reporter genes with a variety of potential cis splicing elements to experimentally probe the functional roles of specific splicing signals; particularly, a method for detecting splice events, comprising the steps of:

providing a reporter construct providing an unconfirmed (e.g. randomized) splice site, wherein formation of a splice junction comprising the splice site yields a first splice form and non-formation of a splice junction comprising the splice site yields a second splice form, wherein the first and second splice forms are, exclusively, a predetermined NMD-targeted splice form or a non-NMD-targeted splice form;
  expressing said construct in a panel of cells, wherein the cells of the panel differ in type or condition, and
  detecting a reporter signal across the panel of cells, wherein the signal is dependent on the relative formation of the first and second splice forms.

IX. NMD Targeted Isoforms in Diseased Cells

The invention provides for the application of any of the foregoing experimental or computational methods in the diagnosis of disease states, such as cancer, and in the development of diagnoses and therapies based on NMD-mediated gene expression regulation. For example, the invention also provides for assaying splice environments as outlined above (VII), wherein said diverse cell types comprise cancer cells and non-cancer cells.

EXEMPLARY PROTOCOLS

To better understand the role of alternative splicing we conducted a large-scale analysis of reliable alternate isoforms of known human genes. We found that one third of the alternative transcripts examined code for early translational termination. We determine that these are targets of nonsense-mediated decay (NMD), a surveillance mechanism that selectively degrades nonsense mRNAs (3–5). Several of these transcripts are from genes for which alternative splicing is known to regulate protein expression by generating alternate isoforms that are differentially subjected to NMD (6,7). Additionally, we observed that simple exon skipping constitutes less than 30% of alternative splices in known genes. Our findings indicate that the coupling of alternative splicing and NMD is a pervasive, underappreciated means of regulating protein expression.

Although studies have shown that alternative splicing plays a major role in generating protein diversity (1, 8, 9), standard analyses may not provide a full appreciation of how alternative splicing modulates gene function. Due to the limitations of the ESTs from which alternative splicing information is commonly derived (10), researchers often restrict their analyses to the simplest splicing modes: exon skipping and mutually exclusive exon usage (8, 11). Similarly, researchers commonly dismiss alternative transcripts that code for early translational termination, since those mRNAs are deemed incapable of generating a functional product. A more complete understanding of alternative splicing requires an unbiased consideration of all alternative mRNA isoforms.

We examined the alternative mRNAs indicated by EST alignments, using a protocol designed to comprehensively identify maximally-reliable sequences that are alternatively spliced (FIG. 1a). To exclude errors from sequencing and assembly, and to simplify the task of determining a reading frame for each transcript, our analysis employed 11984 well-characterized human mRNAs from RefSeq and Locus-Link (12). First, we mapped RefSeq mRNAs to the human genome, requiring that an mRNA align to genomic sequence over the full length of the coding sequence, without gaps in the exons. We further required 98% identity between the coding sequences, favoring RefSeq sequence in cases of nucleotide mismatch. When multiple RefSeq mRNAs aligned to the same region of genomic sequence, we used only the mRNA containing the largest number of exons. To detect alternative isoforms, we aligned 3.9 million EST sequences from dbEST (13) to the genomic sequence and used TAP (14) to infer alternative mRNA splice forms from these alignments (FIG. 1c). Since we used known genes, the reading frame of the canonical mRNA isoforms (i.e., the RefSeq mRNAs) was known. So that the reading frame could be determined for all EST-indicated alternative isoforms, we excluded ESTs whose 5' end aligned to regions of the genomic sequence that did not correspond to coding exons of the RefSeq mRNA. We also excluded cases of intron retention, as these are indistinguishable from incompletely processed transcripts, a common dbEST contaminant. After applying these filters for reliability, this protocol identified 2226 RefSeq mRNAs whose genes undergo alternative splicing to generate 5803 distinct mRNAs. Within this set, we assign higher confidence in splicing events with coverage by multiple ESTs, as these are less likely to result from experimental artifacts in dbEST.

Figure 1D:
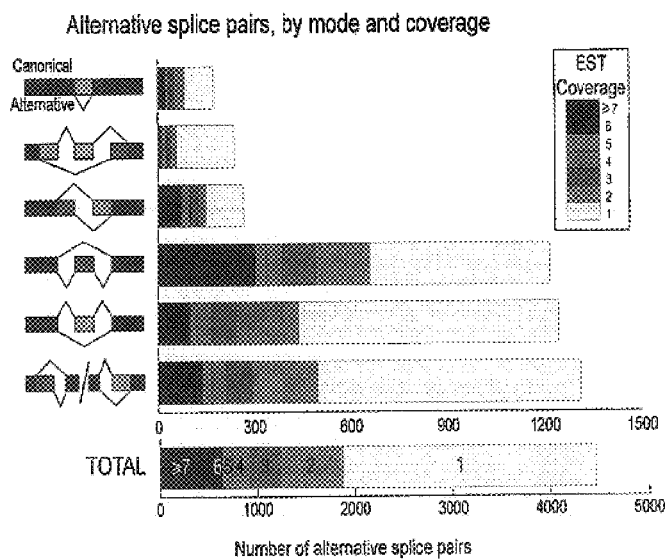
FIG. 1d diagrams alternative splice detection and classification: Alternative splice pairs by mode and coverage.
Figures 1B, 1E:
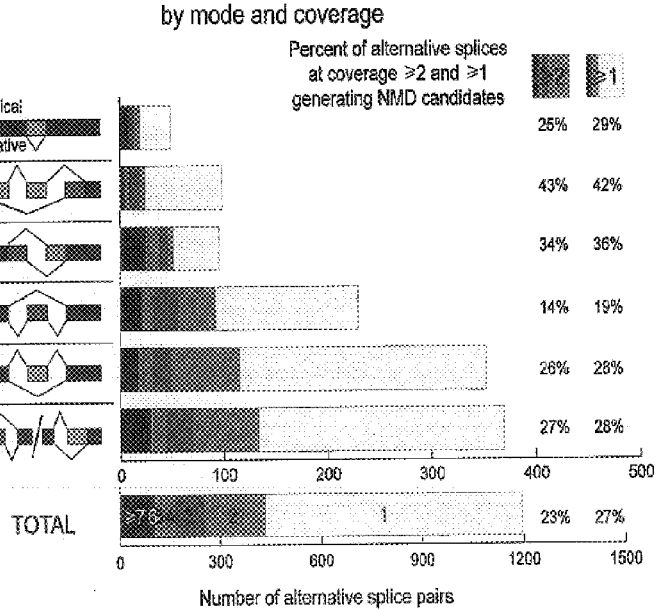
FIG. 1b diagrams alternative splice detection and classification: Splice mode classification.
FIG. 1e diagrams alternative splice detection and classification: Alternative splice pairs generating NMD candidates, by mode and coverage.
Figure 1C:
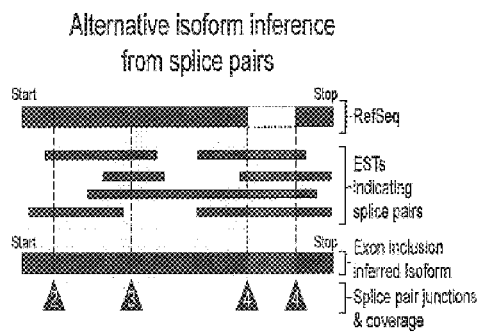
FIG. 1c diagrams alternative splice detection and classification: Alternative isoform inference from splice pairs.

We categorized alternative mRNAs according to exon and splice site usage (FIG. 1b, 1d). Interestingly, simple exon skipping constitutes only 30% of splicing events, and evidence for it becomes relatively less common as we increase the EST coverage threshold. This implies that most alternative splicing of known genes is not simple exon skipping.

We often found that alternative mRNA isoforms would code for truncated proteins. Rather than being intended for translation, our data indicate that many of these are natural targets for nonsense-mediated decay (NMD). Recent work has elucidated the following model for mammalian NMD (4, 5, 15, 16). During mRNA processing, exon-exon splice junctions are marked with exon junction complexes that serve the dual purpose of facilitating export to the cytoplasm and remembering gene structure (17). As translation occurs, the ribosome displaces all exon junction complexes in its path. If a complex remains after a pioneering round of translation (18), a series of reactions ensue, leading to transcript degradation. Thus, transcripts that contain premature termination codons-that is, termination codons more than 50 nucleotides 5' of the final exon-are candidates for NMD. NMD has been shown to occur in all eukaryotes tested, and eukaryotic mRNAs containing premature termination codons are almost always degraded rapidly (19). Consistently, we have observed an extreme bias against known human mRNAs containing premature termination codons: only 2.7% of the RefSeq mRNAs are NMD candidates.

Figure 1F:
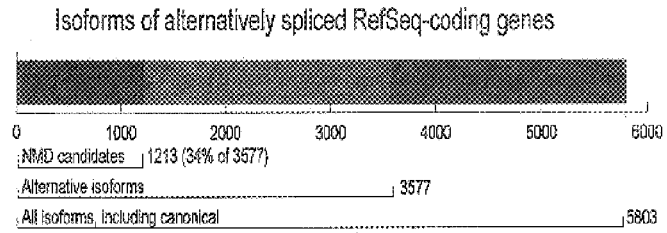
FIG. 1f diagrams alternative splice detection and classification: Isoforms of alternatively-spliced RefSeq-coding genes.

34% of the EST-indicated alternative isoforms in our study contain premature termination codons (FIG. 1f). If these premature termination codons were the result of errors in our analysis, we would expect exon inclusions to be enriched for NMD candidates. This is because perfect exon skipping can only introduce premature termination codons by frameshift, whereas exon inclusions can also introduce them within new coding sequence. Moreover, splice sites and coding sequences for perfect exon skipping are confirmed by a RefSeq mRNA. Yet, in our sample, perfect exon skipping generated premature termination codons more frequently than exon inclusion, and just as frequently as other splicing modes.

For 76% of the mRNA isoforms that are NMD candidates, EST alignments cover a premature termination codon and a splice junction more than 50 nucleotides downstream. In these cases, there is no possibility that additional, undetected splicing events might remove 3' exons thereby preventing termination from being premature. Furthermore, in 80% of these cases, premature termination codons occur in all three reading frames, thus precluding the possibility that an upstream splicing event changed the reading frame from that of the canonical form to prevent premature termination. Finally, we found that the distribution of predicted polyadenylation signals in NMD candidate splices is biased against regions just downstream of premature termination codons, indicating that alternative polyadenylation does not simply stabilize many of the prematurely terminating transcripts.

Our analysis identified 769 genes that undergo alternative splicing to generate 1213 prematurely-terminating alternative mRNA isoforms that are targets of NMD. We conclude that this widespread, deliberate coupling of alternative splicing plays a functional role in regulating protein expression levels and we propose as one model for such regulation analyses of smg mutations in C. elegans (9, 20, 21). Consistently, our analysis turned up several genes known to be regulated by generating isoforms targeted for NMD including GA (22), FGFR2 (7), and the splicing factor AUFI (6). We also found alternatively spliced NMD candidates for six other splicing factors. Besides these, the splicing factor SC35 has been shown to auto-regulate its expression by generating NMD-targeted isoforms (23), though it is excluded from our analysis because its alternative splicing does not affect its coding sequence (FIG. 1A).

Additionally, we found that the human genes for 5 translation factors and 11 ribosomal proteins generate NMD-candidate isoforms. Intriguingly, C. elegans homologs of three of these ribosomal genes-RP3, RP10a, and RP12-generate splice forms that are cleared by NMD (21), indicating that this mode of regulating ribosomal protein expression is evolutionarily conserved.

Since EST libraries are naturally biased against less stable transcripts, mRNAs subjected to NMD should have lower coverage than stable alternative splice forms of the same gene. Therefore, it is striking that many NMD candidates are indicated by multiple ESTs. In light of this bias in dbEST and the fact that splicing in the RefSeq 3' UTR (e.g., in SC35) is excluded from our analysis, we infer that alternative splicing of prematurely-terminating transcripts is even more prevalent than our data indicate.

The coupling of alternative splicing and NMD is easily incorporated into existing models of gene regulation. It allows use of the intrinsic alternative splicing machinery to regulate protein expression in a developmental stage- and cell-specific manner. Moreover, the transcription of genes that will yield unproductive mRNAs is no more wasteful than the transcription of introns, and particularly for genes that require a long time to be transcribed (e.g., dystrophin, which takes 16 hours (24)), post-transcriptional regulation of this sort is readily exploited to provide temporal control unattainable by transcription factors. In light of our findings, we conclude that the contribution of alternative splicing to proteome diversity is balanced by an as-yet unappreciated regulatory role in gene expression.

Mapping RefSeq mRNAs to the Human Genome. Annotations from the January 2002 version of LocusLink (12) were used to associate 11984 human mRNAs from the January 2002 version of RefSeq (12) with contig sequences from the NCBI human genome build 28 (25). The coding regions of the RefSeq mRNAs were aligned against the corresponding contig sequences with the mRNA alignment tool Spidey (26) (FIG. 1a). Because the untranslated regions of the RefSeq mRNAs often aligned poorly to the genomic sequence, we constructed alignments for only the coding portions of the RefSeq mRNAs. Cases where alternative splicing affects the untranslated regions of RefSeq-coding genes (e.g., in SC35) were thus excluded (FIG. 1a).

Aligning EST sequences to genomic sequences. Repetitive elements in the genomic template sequences were masked with RepeatMasker (27). Using WU-BLASTN 2.0 version 2001-06-01 (28), we searched the 3.9 million EST sequences from dbEST (13) version 010402 for matches to the coding exons of the RefSeq mRNA as well as the intervening intron sequences in the human genome. The EST sequences with p-value $<10^{-30}$ were aligned to the genomic sequences using sim4 1.4 (29). Only EST alignments with greater than 93% identity were used.

Alternative isoform inference We used TAP (14) to infer alternative mRNA splice forms from the EST alignments. Since we used known genes, the reading frame of the canonical mRNA isoforms (i.e., the RefSeq mRNAs) was known. So that the reading frame could be determined for all EST-indicated alternative isoforms, we excluded ESTs whose 5' end aligned to regions of the genomic sequence that did not correspond to coding exons of the RefSeq mRNA. We also excluded cases of intron retention, as these are indistinguishable from incompletely processed transcripts, a common dbEST contaminant.

Analysis of canonical and alternative splice pairs. 2226 canonical RefSeq mRNAs were found to have 4452 alternative splice pairs and 3577 alternative mRNA isoforms. Alternative splice pairs are defined as EST-inferred splice junction donor and acceptor sites that differed from those in the canonical RefSeq mRNAs (FIG. 1a). To avoid erroneous alternative splice pair predictions resulting from ambiguity in the alignments surrounding splice junctions, we rejected putative alternative splice pairs found less than 7 bp from a canonical splice pair. Each aligned EST may indicate multiple alternative and canonical splice pairs. Alternative splice pairs within the same mRNA isoform may have varying levels of EST coverage (FIG. 1c). Whenever a splice in an alternative isoform was not covered by ESTs, it was designated canonical.

Classification of alternative splice pairs. Each EST-inferred alternative splice pair was classified according to EST coverage (FIG. 1c), effect on the coding region of the underlying genomic sequence, and exon and splice site usage (FIG. 1d). By this method, mutually exclusive exon usage appeared as exon inclusion. Note that two alternative splice pairs are associated with a single exon inclusion event.

Classification of alternative splicing modes. Alternative splices were categorized according to splice site usage and effects on the coding sequence (FIG. 1b), as described in the figure legend.

Identification of premature translational termination. Premature translational termination was identified when a stop codon occurred more than 50 nucleotides upstream of the final splice junction of an inferred mRNA isoform, and that isoform was labeled as an NMD candidate. The tendency for alternative splicing to introduce premature translational termination may be viewed at the level of alternative splice pairs (FIG. 1e) or alternative mRNA isoforms (FIG. 1f).

Analysis of polyadenylation signals. Polyadq (30) was used to search the alternative mRNAs for polyadenylation sites. On average, a predicted polyadenylation signal occurred once every 2560 nucleotides in the coding exons of the RefSeq mRNAs and the intervening introns. Regions spanning from a premature termination codon to the first splice junction more than 50 nucleotides downstream contained predicted polyadenylation signals once every 3115 nucleotides.

References

1. Modrek, B. & Lee, C. A genomic view of alternative splicing. Nat Genet 30, 13–9 (2002).
2. Smith, C.W. & Valcarcel, J. Alternative pre-mRNA splicing: the logic of combinatorial control. Trends Biochem Sci 25, 381–8 (2000).
3. Hilleren, P. & Parker, R. Mechanisms of mRNA surveillance in eukaryotes. Annu Rev Genet 33, 229–60 (1999).
4. Kim, V. N., Kataoka, N. & Dreyfuss, G. Role of the nonsense-mediated decay factor hUpf3 in the splicing-dependent exon-exon junction complex. Science 293, 1832–1836 (2001).
5. Lykke-Andersen, J., Shu, M. D. & Steitz, J. A. Communication of the position of exon-exon junctions to the mRNA surveillance machinery by the protein RNPS1. Science 293, 1836–1839 (2001).
6. Wilson, G. M. et al. Regulation of AUF1 expression via conserved alternatively spliced elements in the 3' untranslated region. Mol Cell Biol 19, 4056–4064 (1999).
7. Jones, R. B. et al. The nonsense-mediated decay pathway and mutually exclusive expression of alternatively spliced FGFR2IIIb and -IIIc mRNAs. J Biol Chem 276, 4158–67 (2001).
8. Brett, D. et al. EST comparison indicates 38% of human mRNAs contain possible alternative splice forms. FEBS Lett 474, 83–6 (2000).
9. Graveley, B. R. Alternative splicing: increasing diversity in the proteomic world. Trends Genet 17, 100–7 (2001).
10. Thanaraj, T. A. A clean data set of EST-confirmed splice sites from Homo sapiens and standards for clean-up procedures. Nucleic Acids Res 27, 2627–37 (1999).
11. Hide, W. A., Babenko, V. N., van Heusden, P. A., Seoighe, C. & Kelso, J. F. The contribution of exon-skipping events on chromosome 22 to protein coding diversity. Genome Res 11, 1848–53 (2001).
12. Pruitt, K. D. & Maglott, D. R. RefSeq and LocusLink: NCBI gene-centered resources. Nucleic Acids Res 29, 137–40 (2001).

13. Boguski, M. S., Lowe, T. M. & Tolstoshev, C. M. dbEST—database for "expressed sequence tags". Nat Genet 4, 332–3 (1993).
14. Kan, Z., Rouchka, E. C., Gish, W. R. & States, D. J. Gene structure prediction and alternative splicing analysis using genomically aligned ESTs. Genome Res 11, 889–900 (2001).
15. Mitchell, P. & Tollervey, D. mRNA turnover. Curr Opin Cell Biol 13, 320–5 (2001).
16. Cartegni, L., Chew, S. L. & Krainer, A. R. Listening to silence and understanding nonsense: exonic mutations that affect splicing. Nat Rev Genet 3, 285–98 (2002).
17. Le Hir, H., Izaurralde, E., Maquat, L. E. & Moore, M. J. The spliceosome deposits multiple proteins 20–24 nucleotides upstream of mRNA exon-exon junctions. MBO J 19, 6860–9 (2000).
18. Ishigaki, Y., Li, X. J., Serin, G. & Maquat, L. E. Evidence for a pioneer round of mRNA translation: mRNAs subject to nonsense-mediated decay in mammalian cells are bound by CBP80 and CBP20. Cell 106, 607–617 (2001).
19. Nagy, E. & Maquat, L. E. A rule for termination-codon position within intron-containing genes: when nonsense affects RNA abundance. Trends Biochem Sci 23, 198–9 (1998).
20. Morrison, M., Harris, K. S. & Roth, M. B. smg mutants affect the expression of alternatively spliced SR protein mRNAs in Caenorhabditis elegans. Proc Natl Acad Sci U S A 94, 9782–5 (1997).
21. Mitrovich, Q. M. & Anderson, P. Unproductively spliced ribosomal protein mRNAs are natural targets of mRNA surveillance in *C. elegans*. Genes Dev 14, 2173–84 (2000).
22. Labow, B. I., Souba, W. W. & Abcouwer, S. F. Mechanisms governing the expression of the enzymes of glutamine metabolism—glutaminase and glutamine synthetase. J Nutr 131, 2467S-74S (2001).
23. Sureau, A., Gattoni, R., Dooghe, Y., Stevenin, J. & Soret, J. SC35 autoregulates its expression by promoting splicing events that destabilize its mRNAs. EMBO J 20, 1785–96 (2001).
24. Tennyson, C. N., Klamut, H. J. & Worton, R. G. The human dystrophin gene requires 16 hours to be transcribed and is cotranscriptionally spliced. Nat Genet 9, 184–90 (1995).
25. Lander, E. S. et al. Initial sequencing and analysis of the human genome. Nature 409, 860–921 (2001).
26. Wheelan, S. J., Church, D. M. & Ostell, J. M. Spidey: a tool for mRNA-to-genomic alignments. Genome Res 11, 1952–7 (2001).
27. Smit, A. F. A. & Green, P. P RepeatMasker. 0072001 edn (1996–2001).
28. Gish, W. R. WU-BLAST. 2.0 edn (Washington University, St. Louis, 1996–2002).
29. Florea, L., Hartzell, G., Zhang, Z., Rubin, G. M. & Miller, W. A computer program for aligning a cDNA sequence with a genomic DNA sequence. Genome Res 8, 967–74 (1998).
30. Tabaska, J. E. & Zhang, M. Q. Detection of polyadenylation signals in human DNA sequences. Gene 231, 77–86 (1999).

Detailed description of FIG. 1. Alternative splice detection and classification. a, Splice inference. Coding regions of RefSeq mRNAs were aligned to genomic sequence to determine canonical splicing patterns. EST alignments to genomic sequence confirmed the canonical splices and indicated alternative splices. Canonical (RefSeq) splices are indicated above the exons while alternative splices are indicated below the exons. When an alternative splice introduced a stop codon more than 50 nucleotides upstream of the final exon-exon splice junction of an inferred mRNA isoform, the stop codon was classified as premature and the corresponding mRNA isoform was labeled a NMD candidate. In the example shown, an exon skip caused a frameshift, resulting in the introduction of a premature stop codon. Restricting the analysis to coding regions assured high alignment quality, but this excluded alternative splicing in non-coding regions, such as occurs with splicing factor SC35. Intron retentions were also excluded, since ESTs indicating intron retention are indistinguishable from incompletely-processed transcripts, a common dbEST contaminant. b, Splice mode classification. Alternative splices were categorized according to splice site usage and effects on the coding sequence. Splice sites introduced shows the number of splice donor/acceptor sites that were observed in the alternative splice, but were not included in the canonical splice. Splice sites lost shows the number of splice donor/acceptor sites that were included in the canonical splice and absent in the alternative splice. Coding region change indicates whether an alternative splice added (red) or subtracted (green) coding sequence to the alternative isoform relative to the canonical isoform. By our method, mutually-exclusive exon usage appears as exon inclusion. Our analysis excluded intron retentions, which would be classified as: 0 splice sites introduced, 2 sites lost, and addition of coding sequence. c, Alternative isoform inference from splice pairs. Splice pairs are splice donor/acceptor sites (▲) inferred from the alignments. Alternative splice pairs are those indicated by ESTs, but not by a RefSeq mRNA. The exon composition of an isoform was determined from EST-demonstrated splice pairs, which may be covered by multiple ESTs. Coverage of splice pairs is indicated in each ▲. Coverage for a complete isoform is not meaningful because of variability in coverage of its splice pairs. d, Alternative splice pairs by mode and coverage. The total number of alternative splice pairs associated with each splicing mode is shown at various levels of EST coverage. The distance from the y-axis to the right edge of each box corresponds to the total number of splice pairs with coverage greater than or equal to the number indicated. Note that each exon inclusion event involves two splice pairs. e, Alternative splice pairs generating NMD candidates, by mode and coverage. The subset of alternative splice pairs producing premature termination codons is involved in generating NMD-candidate mRNA isoforms. Numbers of splice pairs are displayed as in d. Also shown are the NMD-candidate splice pairs at coverage $\geq 1$ and $\geq 2$ as a percentage of all alternative splice pairs for each splicing mode. f, Isoforms of alternatively-spliced RefSeq-coding genes. Shown are the total numbers of isoforms of the RefSeq-coding genes for which alternative isoforms were found. These are subdivided into the following categories: all isoforms including canonical; alternative isoforms (i.e., all isoforms excluding canonical); and NMD candidates.

All publications and patent applications cited in this specification and all references cited therein are herein incorporated by reference as if each individual publication or patent application or reference were specifically and individually indicated to be incorporated by reference.

Any material accompanying this application on compact disc or other recorded medium is incorporated by reference, including the following files recorded on accompanying compact discs #1–#4 (each provided in duplicate, Copy 1 and Copy 2):

COMPACT DISC INVENTORY (all files listed are text files, excluding .Z and .gz files, which are compressed text files)

| FILENAME | KB | DATE | DESCRIPTION |
|---|---|---|---|
| | Disc #1 [isoform dataset, software tools] | | |
| aln_refseq.pl | 5 | May 28, 2002 5:27 PM | see, README.src |
| build_altspl.pl | 13 | May 28, 2002 5:27 PM | see, README.src |
| calc_isoform_stats.pl | 9 | May 28, 2002 5:27 PM | see, README.src |
| cgap_ests.pl | 5 | May 28, 2002 5:27 PM | see, README.src |
| check.ptcs.pl | 4 | May 28, 2002 5:27 PM | see, README.src |
| cluster_contigs.pl | 6 | May 28, 2002 5:27 PM | see, README.src |
| contig_overlaps.pl | 2 | May 28, 2002 5:27 PM | see, README.src |
| format_contigs.pl | 2 | May 28, 2002 5:27 PM | see, README.src |
| map_refseqs.pl | 8 | May 28, 2002 5:27 PM | see, README.src |
| map.refseqs-CDS.pl | 7 | May 28, 2002 5:27 PM | see, README.src |
| parse_refseq.aln.pl | 6 | May 28, 2002 5:27 PM | see, README.src |
| polyA_stats.pl | 5 | May 28, 2002 5:27 PM | see, README.src |
| README.src | 5 | May 28, 2002 5:27 PM | see, README.src |
| retrieve_coding_refseq.pl | 2 | May 28, 2002 5:27 PM | see, README.src |
| retrieve_estid.pl | 4 | May 28, 2002 5:27 PM | see, README.src |
| rm_single_exons.pl | 2 | May 28, 2002 5:27 PM | see, README.src |
| strand_overlap.pl | 2 | May 28, 2002 5:27 PM | see, README.src |
| test_coverage.pl | 9 | May 28, 2002 5:27 PM | see, README.src |
| README.isoforms | 5 | May 28, 2002 5:28 PM | description of the isoform dataset file, isoforms.altspl.fa |
| README.src | 5 | May 28, 2002 5:28 PM | description of the software files in the src/directory |
| README.refseq | 7 | May 28, 2002 5:28 PM | description of the NCBI RefSeq database |
| README.locuslink | 26 | May 28, 2002 5:28 PM | description of the NCBI LocusLink database |
| README.dbEST | 14 | May 28, 2002 5:28 PM | description of the NCBI dbEST database |
| README.genome | 11 | May 28, 2002 5:28 PM | description of the NCBI Human Genome database |
| isoforms.altspl.fa | 23916 | May 28, 2002 5:28 PM | sequence and splice site information for all alternative isoforms |
| Alt_and_NMD_isoforms_list.txt | 188 | May 28, 2002 5:28 PM | listing ID's for all alternative isoforms in isoforms.altspl.fa |
| INVENTORY.doc | 35 | May 28, 2002 5:29 PM | Microsoft Word version of CD inventory |
| INVENTORY.txt | 3 | May 28, 2002 5:28 PM | Text version of CD inventory |
| | Disc #2 [dbEST 010402] | | |
| est_human.Z | 641,539 | May 28, 2002 4:58 PM | NCBI dbEST version 010402 |
| | Disc #3 [NCBI human genome, build 28 - part 1 (Chr. 1–10)] | | |
| hs_chr1.fa.Z | 68,532 | May 28, 2002 4:16 PM | Human chromosome 1 sequence |
| hs_chr2.fa.Z | 67,755 | May 28, 2002 4:17 PM | Human chromosome 2 sequence |
| hs_chr3.fa.Z | 56,351 | May 28, 2002 4:18 PM | Human chromosome 3 sequence |
| hs_chr4.fa.Z | 52,245 | May 28, 2002 4:18 PM | Human chromosome 4 sequence |
| hs_chr5.fa.Z | 51,138 | May 28, 2002 4:19 PM | Human chromosome 5 sequence |
| hs_chr6.fa.Z | 51,686 | May 28, 2002 4:20 PM | Human chromosome 6 sequence |
| hs_chr7.fa.Z | 46,298 | May 28, 2002 4:20 PM | Human chromosome 7 sequence |
| hs_chr8.fa.Z | 40,370 | May 28, 2002 4:21 PM | Human chromosome 8 sequence |
| hs_chr9.fa.Z | 33,863 | May 28, 2002 4:22 PM | Human chromosome 9 sequence |
| hs_chr10.fa.Z | 39,638 | May 28, 2002 4:22 PM | Human chromosome 10 sequence |
| | Disc #4 [NCBI human genome, build 28 - pt 2 (Chr. 10–22, X, Y), NCBI RefSeq and LocusLink databases]] | | |
| hs_chr11.fa.Z | 40,603 | Apr. 21, 2002 10:38 PM | Human chromosome 11 sequence |

| FILENAME | KB | DATE | DESCRIPTION |
| --- | --- | --- | --- |
| hs_chr12.fa.Z | 38,857 | Apr. 21, 2002 10:39 PM | Human chromosome 12 sequence |
| hs_chr13.fa.Z | 29,317 | Apr. 21, 2002 10:40 PM | Human chromosome 13 sequence |
| hs_chr14.fa.Z | 26,246 | Apr. 21, 2002 10:41 PM | Human chromosome 14 sequence |
| hs_chr15.fa.Z | 23,806 | Apr. 21, 2002 10:42 PM | Human chromosome 15 sequence |
| hs_chr16.fa.Z | 22,723 | Apr. 21, 2002 10:42 PM | Human chromosome 16 sequence |
| hs_chr17.fa.Z | 23,510 | Apr. 21, 2002 10:43 PM | Human chromosome 17 sequence |
| hs_chr18.fa.Z | 23,340 | Apr. 21, 2002 10:44 PM | Human chromosome 18 sequence |
| hs_chr19.fa.Z | 16,834 | Apr. 21, 2002 10:44 PM | Human chromosome 19 sequence |
| hs_chr20.fa.Z | 17,770 | Apr. 21, 2002 10:45 PM | Human chromosome 20 sequence |
| hs_chr21.fa.Z | 10,000 | Apr. 21, 2002 10:45 PM | Human chromosome 21 sequence |
| hs_chr22.fa.Z | 10,113 | Apr. 21, 2002 10:45 PM | Human chromosome 22 sequence |
| hs_chrX.fa.Z | 42,293 | Apr. 21, 2002 10:47 PM | Human chromosome X sequence |
| hs_chrY.fa.Z | 6,619 | Apr. 21, 2002 10:47 PM | Human chromosome Y sequence |
| refseq_0102.fa | 37,936 | Apr. 21, 2002 12:29 PM | NCBI RefSeq Human mRNA database |
| LL_hs.out.gz | 1,221 | Apr. 17, 2002 12:29 PM | NCBI LocusLink database |
| LL_tmpl.gz | 13,980 | Apr. 17, 2002 8:12 PM | NCBI LocusLink database |

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A computational method for systematically identifying alternative mRNA splice isoforms of known genes, the method comprising the steps of:
   a) identifying target gene sequences by mapping mRNA sequences of an mRNA sequence dataset to genomic sequences of a genomic DNA sequence dataset, wherein:
   each mRNA sequence is required to align to a corresponding genomic sequence over the full length of the coding sequence of the mRNA sequence, without gaps in the exons of the genomic sequence; and
   at least 98% identity between each mRNA sequence and the corresponding genomic sequence is required, favoring the mRNA sequence in case of nucleotide mismatch; and
   b) identifying a dataset of alternate mRNA splice isoforms of the target gene sequences by aligning EST sequences from an EST sequence dataset to the target gene sequences and using a transcript assembly protocol, wherein:
   the alternative mRNA splice isoform dataset is restricted to mRNA sequences in which the 5' end of an EST sequence aligns to a coding sequence of the corresponding mRNA sequence, such that the reading frame of the coding sequences can be determined for all isoforms of the dataset, and
   isoforms presenting intron retention are excluded from the alternative mRNA splice isoform dataset, and
   coverage by multiple EST sequences is required for each splicing event.

2. A computational method according to claim 1, further comprising the step of identifying a subset of the alternative mRNA splice isoform dataset consisting of isoforms subject to nonsense-mediated decay (NMD), comprising:
   screening the alternative mRNA splice isoform dataset for a subset of isoforms comprising alternate splices which introduce a stop codon more than 50 bp upstream of the final exon-exon splice junction, and classifying such subset isoforms as comprising premature stop codons and as targets of NMD.

3. A computational method according to claim 1, further comprising the step of correlating the alternatively spliced isoforms with their relative expression in cancer cells and non-cancer cells.

4. A computational method according to claim 2, further comprising the step of correlating the alternatively spliced isoforms with their relative expression in cancer cells and non-cancer cells.

* * * * *